United States Patent [19]

Nichols et al.

[11] Patent Number: 4,507,478

[45] Date of Patent: Mar. 26, 1985

[54] 2-MERCAPTOPYRIMIDOHEXAHYDROQUINOLINES AND RELATED COMPOUNDS

[75] Inventors: Cynthia L. Nichols; Edmund C. Kornfeld; John M. Schaus, all of Indianapolis, Ind.

[73] Assignee: Eli Lilly and Company, Indianapolis, Ind.

[21] Appl. No.: 535,518

[22] Filed: Sep. 26, 1983

[51] Int. Cl.³ ................. C07D 487/17; C07D 215/00; A61K 7/42
[52] U.S. Cl. ..................................... 544/250; 424/59; 546/164; 546/165
[58] Field of Search ........................ 544/250; 424/251

[56] References Cited

U.S. PATENT DOCUMENTS 4,198,415 4/1980 Kornfeld et al. .................... 546/158

OTHER PUBLICATIONS

Modest, J. Org. Chem. 30, 1837, (1965).
Boger, J. Org. Chem., 1982, 47, pp. 2673–2675.

*Primary Examiner*—Donald G. Daus
*Assistant Examiner*—Cecilia Shen
*Attorney, Agent, or Firm*—James L. Rowe; Arthur R. Whale

[57] ABSTRACT

Trans-(±) or trans-(−)-2,4-permissibly-substituted-6-alkyl or allyl octahydropyrimido[4,5-g]quinolines and related compounds, ultraviolet light absorbers.

11 Claims, No Drawings

2-MERCAPTOPYRIMIDOHEXAHYDROQUINO-LINES AND RELATED COMPOUNDS

BACKGROUND OF THE INVENTION

This invention relates to trans(±) or trans(−)-octahydropyrimido[4,5-g]quinolines of the formulas

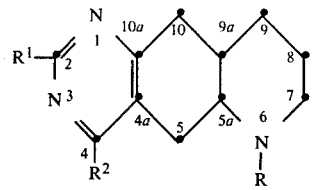

and

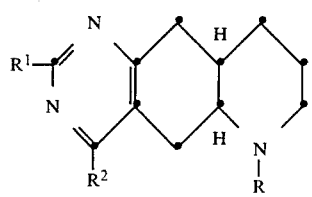

wherein R is H, CN and $C_1$–$C_3$ alkyl or allyl; $R^1$ is H, OH, SH, O-$C_1$–$C_3$ alkyl, S-$C_1$–$C_3$ alkyl or $NH_2$; $R^2$ is H, OH or $NH_2$ with the proviso that $R^1$ can only be $NH_2$ when $R^2$ is OH or $NH_2$; and acid addition salts thereof made from non-toxic acids. Formula I is named as a trans-(±)-6-substituted-2,4-permissibly-substituted-5,5a,6,7,8,9,9a,10-octahydropyrimido[4,5-g]quinoline and formula II is the corresponding trans-(−)-enantiomer.

Preferred subgroups of compounds represented by I or II above include:

(a) compounds in which R is $C_1$–$C_3$ alkyl;
(b) compounds in which R is n-propyl;
(c) compounds in which $R^2$ is H; and
(d) compounds in which $R^1$ is SH or S-$C_1$–$C_3$ alkyl.

The compounds represented by formulas I and II absorb ultraviolet light with absorption peaks in the range 265–350 mu, (which range encompasses the UVA—280–300 mu range—) and are therefore potentially useful as sunscreen agents. The compounds are also useful as intermediates, as will be more fully developed hereinafter.

Compounds according to I or II in which $R^1$ is SH or S-$C_1$–$C_3$ alkyl and $R^2$ is H are prepared by reacting thiourea or an S-$C_1$–$C_3$ alkyl isothiourea with a compound of the formula III or IV

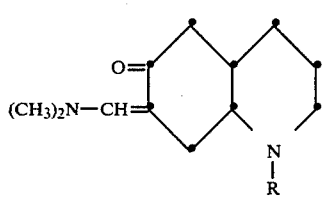

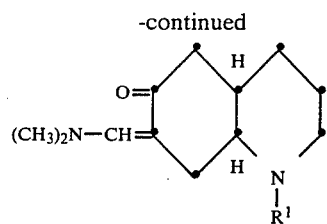

Compounds according to I and II wherein $R^2$ is H and $R^1$ is OH are prepared by acidic hydrolysis of a trans-(±) or trans-(−)-2-$C_1$–$C_3$ alkylthio-6-$C_1$–$C_3$ alkyl or allyl-5,5a,6,7,8,9,9a,10-octahydropyrimido[4,5-g]quinoline. The product of this reaction, a 2-OH derivative, can be readily alkylated by standard etherification reactions; e.g., dimethylsulfate and base, to yield the 2-$C_1$–$C_3$ alkoxy derivatives; e.g., a 2-methoxy derivative, according to I or II.

Compounds according to I or II in which $R^1$ is $NH_2$ and $R^2$ is OH are prepared by reacting a 1-alkyl or allyl-6-oxo-7-alkoxycarbonyldecahydroquinoline (furnished by the procedure of Schaus, Huser and Booher, Ser. No. 535,519, filed Sept. 26, 1983, whereby a trans-(±) or trans-(−)-6-oxo-1-$C_1$–$C_3$ alkyl or allyldecahydroquinoline is reacted with a dialkyl carbonate in the presence of sodium hydride in an inert mutual solvent, with a guanidine salt. After work-up of the reaction mixture, the 2-amino-4-hydroxy derivative thus formed is isolated by standard means.

Compounds according to I or II in which both $R^1$ and $R^2$ are $NH_2$ are prepared by cyclizing the usual trans-(±) or trans-(−)-1-substituted-6-oxodecahydroquinoline with cyanoguanidine in a high boiling mutual inert solvent such as CARBITOL—see Modest et al., *J. Org. Chem.*, 30, 1837 (1965). When $R^1$ and $R^2$ are H, a different cyclization reaction is employed to join the pyrimidine ring to a 1-$C_1$–$C_3$ alkyl or allyl decahydroquinoline nucleus. The procedure of Boger et al. *J. Org. Chem.*, 47, 2673 (1982) was adapted to the specific synthetic goal. This procedure involves the reaction of a cyclic ketone with pyrrolidine to form an enamine (Formula V or VI below), reaction of which with 1,3,5-triazine yields an unsubstituted pyrimidine ring fused to the decahydroquinoline.

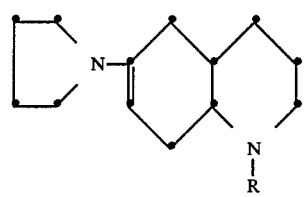

and

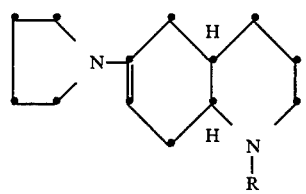

wherein R is $C_1$–$C_3$ alkyl or allyl.

An illustrative reaction from Boger is that of cyclohexanone with pyrrolidine to form a 1-pyrrolidino-1-cyclohexene which, on treatment with 1,3,5-triazine yields tetrahydroquinazoline. In our reaction, the trans-(±) or trans-(−)-1-$C_1$-$C_3$ alkyl or allyl-6-oxodecahydroquinoline is the starting ketone which forms the enamine with pyrrolidine.

While compounds according to I and II in which R is $C_1$-$C_3$ alkyl or allyl are the primary products of this invention, those compounds in which R is H or CN are not only UV absorbers but are also intermediates for the preparation of compounds carrying a different alkyl group (from that of the 6-oxodecahydroquinoline starting material) or an allyl group. For example, if it is desired to prepare a compound according to I or II in which R is allyl, it is possible (depending on the nature of the $R^1$ and $R^2$ substituents) to replace the R alkyl group with CN (using CNBr), and then to remove the CN group by hydrolysis to yield compounds wherein R is H. This secondary amine derivative can then be allylated as with allyl chloride or can be reductively alkylated with an aldehyde or can be alkylated with a $C_1$-$C_3$ alkyl halide to yield a compound according to I or II having an allyl group or a different alkyl at N-6. Incidentally, it is not necessary to replace an N-methyl with a different alkyl group in order for the above process to be useful. For example, it is possible to replace a $CH_3$ group with a $^{13}CH_3$ containing an isotopically-tagged carbon. Preferably, however, because of the reactivity of SH and OH groups at C-2 in I or II to CNBr, the interchange of groups on the quinoline nitrogen should take place prior to ring closure; i.e., at the 6-oxodecahydroquinoline stage. In this procedure, a trans-(±) or trans-(−)-1-methyl-6-oxodecahydroquinoline, for example, is transformed to the 1-cyano compound—see Bach et al., *J. Med. Chem.*, 23, 481 (1980) or U.S. Pat. No. 4,198,415. Acidic hydrolysis or hydrogenolysis of this compound by the methods of Titus and Bach, Ser. No. 535,522, filed Sept. 26, 1983, yields trans-(±) or trans-(−)-6-oxodecahydroquinoline. This secondary amine can then be allylated or realkylated possibly with a tagged alkyl, using allyl or alkyl halides to prepare the desired intermediate trans-(±) or trans-(−)-1-allyl or alkyl-6-oxodecahydroquinoline. The above procedures are clearly extremely useful in preparing the difficult-to-obtain N-allyl derivatives because the best procedures for obtaining the 2-alkyl-6-oxodecahydroquinolines involves multiple reduction or hydrogenation procedures, and an allyl group would not survive all of these synthetic steps.

The following specific examples more fully illustrate the preparative aspects of this invention.

EXAMPLE 1

Preparation of trans-(±)-2-mercapto-6-n-propyl-5,5a,6,7,8,9,9a,10-octahydropyrimido[4,5-g]quinoline One gram of trans-(±)-1-n-propyl-6-oxo-7-dimethylaminomethylenedecahydroquinoline was reacted with 0.33 g. of thiourea in 20 ml. of ethanol by refluxing overnight under a nitrogen atmosphere. The volatile constituents were removed in vacuo to yield trans-(±)-2-mercapto-6-n-propyl-5,5a,6,7,8,9,9a,10-octahydropyrimido[4,5-g]quinoline free base. The free base was converted to the dihydrochloride salt by standard procedures to yield 0.17 g. of dihydrochloride salt melting at 267°–277° C. after recrystallization from methanol.

Analysis Calculated: C, 49.99; H, 6.84; N, 12.49; Found: C, 49.52; H, 6.87; N, 12.33; Molecular ion at 263.

Following the above procedure but employing S-methylthiourea, trans-(±)-2-methylthio-6-n-propyl-5,5a,6,7,8,9,9a,10-octahydropyrimido[4,5-g]quinoline was prepared, and the free base, obtained by chromatography over florisil using methylene dichloride as the eluant, was converted to the monohydrochloride salt to yield 0.34 g. of a white fluffy solid (from 2.7 g. starting decahydroquinoline) having a molecular ion at 277 with the following analysis.

Analysis Calculated: C, 57.40; H, 7.71; N, 13.39; S, 10.21 Found: C, 57.73; H, 7.83; N, 13.58; S, 10.09.

EXAMPLE 2

Preparation of trans-(±)-2-hydroxy-6-n-propyl-5,5a,6,7,8,9,9a,10-octahydropyrimido[4,5-g]quinoline A mixture of 0.93 g. of trans-(±)-2-methylthio-6-n-propyl-5,5a,6,7,8,9,9a,10-octahydropyrimido[4,5-g]quinoline and 2 ml. of 12N aqueous hydrochloric acid was heated to reflux temperature for 1.5 hours. The reaction mixture was then concentrated in vacuo. Methanol was added and the reaction mixture again concentrated in vacuo. A residual green oil, comprising trans-(±)-2-hydroxy-6-n-propyl-5,5a,6,7,8,9,9a,10-octahydropyrimido[4,5-g]quinoline dihydrochloride formed in the above reaction was dissolved in a mixture of ethyl acetate and ethanol. As the green oil dissolved, crystals formed. Trans-(±)-2-hydroxy-6-n-propyl-5,5a,6,7,8,9-,9a,10-octahydropyrimido[4,5-g]quinoline dihydrochloride thus prepared had the following physical characteristics: $R_f$(methanol)=0.5; molecular ion at 247; yield=0.62 g.

Analysis Calculated: C, 52.50; H, 7.24; N, 13.12; Found: C, 52.29; H, 7.08; N, 12.88.

EXAMPLE 3

Preparation of trans-(±)-2-methoxy-6-n-propyl-5,5a,6,7,8,9,9a,10-octahydropyrimido[4,5-g]quinoline Following the procedure of Example 1, a reaction mixture was prepared from trans-(±)-1-n-propyl-6-oxo-7-dimethylaminomethylenedecahydroquinoline and O-methylisourea hydrogen sulfate in 20 ml. of anhydrous ethanol. The reaction mixture was heated to reflux temperature overnight and was then evaporated to dryness. The resulting residue was dissolved in chloroform. The chloroform solution was chromatographed over florisil using chloroform containing increasing amounts (0–15%) of methanol as the eluant. Fraction 5 was shown by tlc to contain trans-(±)-2-methoxy-6-n-propyl-5,5a,6,7,8,9,9a,10-octahydropyrimido[4,5-g]quinoline formed in the above reaction. The solvent was removed in vacuo leaving a residual yellow oil. The yellow oil was dissolved in methanol and the methanolic solution saturated with gaseous hydrogen chloride. Ethyl acetate was added to the hot methanol solution to the point of incipient precipitation. Upon cooling, yellow crystals of trans-(±)-2-methoxy-6-n-propyl-5,5a,6,7,8,9,9a,10octahydropyrimido[4,5-g]quinoline dihydrochloride formed which were collected by filtration. The product had a molecular ion at 261.

EXAMPLE 4

Preparation of trans-(±)-6-n-propyl-5,5a,6,7,8,9,9a,10-octahydropyrimido[4,5-g]quinoline Four grams of trans-(±)-1-n-propyl-6-oxodecahydroquinoline and 8 ml. of pyrrolidine were refluxed in cyclohexane solution under a nitrogen atmosphere in an apparatus equipped with a Dean-Stark trap. Heating was continued until water collection in the trap had stopped. The reaction mixture was then cooled and concentrated to dryness in vacuo. The pyrrolidine enamine, trans-(±)-1-n-propyl-6-pyrrolidino-1,2,3,4,4a,5,8,8a-octahydroquinoline, having an absorption maximum in the infrared at 1637 cm$^{-1}$ and negligible absorption at 1708 cm$^{-1}$, was treated with a solution of 1.8 g. of 1,3,5-triazine in 30 ml. of dioxane. The reaction mixture was heated to reflux temperature under a nitrogen blanket for 48 hours. TLC at this point indicated that some reaction had taken place. The reaction mixture was concentrated in vacuo. An aqueous solution of sodium bisulfite was added to the residual dark oil. Methylene dichloride was then added and the subsequent mixture stirred under a nitrogen blanket for about one hour. Additional methylene dichloride and water were added and the layers separated. The aqueous layer was extracted twice with equal volumes of methylene dichloride and the methylene dichloride extracts combined. The combined extracts were dried and the methylene dichloride removed therefrom in vacuo to yield 2 g. of a crude product which showed a major spot on tlc: Rf=0.44; 9:1 chloroform/methanol containing trace amounts of ammonia as the eluant. Chromatography over florisil yielded 1.14 g. of a dark oil which was further purified by vacuum distillation. The distillate was dissolved in ethanol and gaseous HCl bubbled into the ethanol solution. Evaporation of the volatile constituents in vacuo yielded a residue which was dissolved in ethanol. Ether was added to the point of incipient precipitation and the solution cooled to yield ultimately 0.82 g. of a crude dihydrochloride salt. Recrystallization of the salt from ethanol yielded 0.22 g. of trans-(±)-6-n-propyl-5,5a,6,7,8,9,9a,10-octahydropyrimido[4,5-g]quinoline dihydrochloride.

Analysis (after drying at 120° C.) Calculated: C, 55.27; H, 7.62; N, 13.81; Cl, 23.30 Found: C, 55.52; H, 7.37; N, 13.52; Cl, 23.40.

Trans-(−)-6-n-propyl-5,5a,6,7,8,9,9a,10-octahydropyrimido[4,5-g]quinoline is prepared in analogous fashion starting with trans-(−)-1-n-propyl-6-oxodecahydroquinoline.

EXAMPLE 5

Preparation of trans-(±)-2-amino-4-hydroxy-6-n-propyl-5,5a,6,7,8,9,9a,10-octahydropyrimido[4,5-g]quinoline A reaction mixture was prepared from 2.0 g. of trans-(±)-1-n-propyl-6-oxo-7-ethoxycarbonyldecahydroquinoline (prepared by the method of Schaus, Huser and Booher—loc. cit.), 20 ml. of anhydrous ethanol and 0.67 g. of guanidine carbonate. The reaction mixture was heated to reflux temperature overnight under a nitrogen atmosphere. The white precipitate which formed was collected by filtration and the filter cake washed with ethanol and dried; yield=1.36 g. The filter cake was dissolved in 52 ml. of 0.1N aqueous hydrochloric acid. The acidic mixture was filtered and the filtrate concentrated in vacuo. The solid residue which formed was dissolved in boiling methanol. The methanol solution was filtered and trans-(±)-2-amino-4-hydroxy-6-n-propyl-5,5a,6,7,8,9,9a,10-octahydropyrimido[4,5-g]quinoline hydrochloride thus prepared crystallized from the filtrate to yield 0.79 g. of product. The free base had the following physical characteristics: mass spectrum, molecular ion at 262.

Analysis Calculated: C, 64.08; H, 8.45; N, 21.36; Found: C, 64.18; H, 8.51; N, 21.13.

The hydrochloride salt had the following physical characteristic: mass spectrum, molecular ion at 262.

EXAMPLE 6

Preparation of trans-(±)-2,4-diamino-6-n-propyl-5,5a,6,7,8,9,9a,10-octahydropyrimido[4,5-g]quinoline A reaction mixture was prepared from 5 g. of trans-(±)-1-n-propyl-6-oxodecahydroquinoline and 3.24 g. of cyanoguanidine in 12.5 ml. of diethyleneglycol monoethylether (CARBITOL). The reaction mixture was heated to reflux temperature under an N$_2$ atmosphere for about 6 hours, and was then poured into a mixture of very dilute aqueous NaOH and ethyl acetate. A tan solid precipitated which was collected by filtration. Recrystallization of the filter cake from a methanol-ethyl acetate solvent mixture yielded 1.50 g. (22% yield) of a white powder melting at 238°–240° C. with decomposition. Trans-(±)-2,4-diamino-6-n-propyl-5,5a,6,7,8,9,9a,10-octahydropyrimido[4,5-g]quinoline thus prepared had the following physical characteristics:

Infrared spectrum, at 3385, 3163, 1630, 1593, 1569, 1441 Ultraviolet spectrum (methanol); peaks at 201, 212, 228, 283 Mass spectrum: peaks at 261, 218, 138, 125, 124, 96.

Analysis Calculated: C, 64.33; H, 8.87; N, 26.80 Found: C, 64.32; H, 8.75; N, 27.03.

A dihydrochloride salt was prepared and recrystallized from methanol/ethyl acetate to yield a white powder melting above 250° C. The salt had the following elemental analysis.

Analysis Calculated: C, 50.30; H, 7.54; N, 20.95; Cl, 21.21 Found: C, 50.03; H, 7.34; N, 20.67; Cl, 21.32.

In addition to their use as potential ultraviolet light absorbers, the compounds of this invention also serve as intermediates. Examples of such use are contained in the above synthetic procedures; i.e., the 2-OH derivative is prepared from a 2-methylthio compound or a 2-methoxy derivative by methylation of a 2-hydroxy derivative. Additionally, a 2-hydroxy group can be replaced directly with dimethylamine or monomethylamine to yield trans-(±) or trans-(−)-2-dimethylamino or methylamino-6-alkyl or allyloctahydropyrimido[4,5-g]quinoline disclosed and claimed in the copending application of Nichols and Kornfeld, Ser. No. 535,503, filed Sept. 26, 1983. Additionally, the 2-OH group can be reacted directly, or via a 2-chloro group, with ammonia or sodamide to yield a 2-amino derivative.

In employing the compounds of this invention as ultraviolet light absorbers or sunscreen agents, a compound according to I or II is incorporated into a cream base having the following ingredients:

| CREAM BASE I | |
| --- | --- |
| Ingredient | % by Weight |
| Cetyl alcohol | 3.5 |
| Lanolin | 3.5 |

-continued
CREAM BASE I

| Ingredient | % by Weight |
|---|---|
| Polysorbate 60[1] | 4.0 |
| Falba absorption base[2] | 0.5 |
| Carbopol 934[3] | 0.06 |
| Sorbitan monostearate | 2.6 |
| Anhydrous citric acid | 0.07 |
| Methyl paraben | 0.2 |
| Propyl paraben | 0.15 |
| Ten or IV[4] | |
| Isopropyl myristate | 12 |
| Cloroicil 200[5] | 0.2 |
| 98% triethanolamine | 0.17 |
| Sunscreen agent | up to 5.0 |
| Fragrance | 0–0.3 |
| Water q.s. to | 100 |

[1] polyoxyethylene (20) sorbitan mono-oleate.
[2] a mixture of mineral oil, lanolin, lanolin alcohol, paraffin and beeswax.
[3] a cross-linked acrylic acid polymer.
[4] a mixture of corn oil, BHT-(2,6-di-t-butyl-6-methylphenol) and BHA (t-butyl-p-methoxyphenol).
[5] cis-isomer of 1-(3-chloroallyl)-2,5,7-triaza-1-azonia adamantane chloride.

CREAM BASE II

| Ingredient | % by Weight |
|---|---|
| Isopropylmyristole | 13.5 |
| Mineral oil | 8.00 |
| 70% Sorbitol solution | 7.50 |
| Triglyceryldiisosterate | 5.50 |
| Beeswax | 4.00 |
| Polyethylene | 4.00 |
| Bentone #38[1] | 1.5 |
| Imidazolinylurea | 0.40 |
| Sodium tetraborate | 0.38 |
| Propylparaben | 0.20 |
| Methylparaben | 0.20 |
| Fragrance material | 0–.30 |
| Sunscreen agent | 1–5 |
| Water q.s. to | 100 |

[1] Reaction product of bentonite and a quaternary ammonium halide [$(CH_3)_2R_2N$] + $Cl^-$ where R is a tallow fatty radical

We claim:

1. A trans-($\pm$) compound of the formula

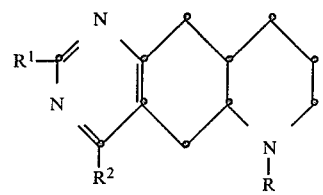

or a trans-(−) compound of the formula

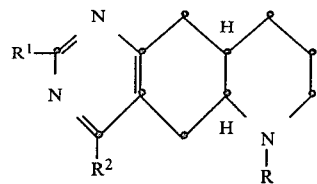

wherein R is $C_1$–$C_3$ alkyl, allyl, H or CN; $R^1$ is H, $NH_2$, SH, S-$C_1$–$C_3$ alkyl, OH or O-$C_1$–$C_3$ alkyl; $R^2$ is H, OH or $NH_2$ subject to the proviso that $R^1$ can only be $NH_2$ when $R^2$ is $NH_2$ or OH, and pharmaceutically-acceptable salts thereof.

2. A compound according to claim 1 in which R is n-propyl.

3. A compound according to claim 1 in which $R^2$ is H.

4. A compound according to claim 2 in which $R^1$ is SH or S-$C_1$–$C_3$ alkyl.

5. A compound according to claim 1, said compound being trans-($\pm$)-2-mercapto-6-n-propyl-5,5a,6,7,8,9,9a,10-octahydropyrimido[4,5-g]quinoline.

6. A compound according to claim 1, said compound being trans-($\pm$)-2-methylthio-6-n-propyl-5,5a,6,7,8,9,9a,10-octahydropyrimido[4,5-g]quinoline.

7. A compound according to claim 1, said compound being trans-($\pm$)-2,4-diamino-6-n-propyl-5,5a,6,7,8,9,9a,10-octahydropyrimido[4,5-g]quinoline.

8. A compound according to claim 1, said compound being trans-($\pm$)-6-n-propyl-5,5a,6,7,8,9,9a,10-octahydropyrimido[4,5-g]quinoline.

9. A compound according to claim 1, said compound being trans-(−)-6-n-propyl-5,5a,6,7,8,9,9a,10-octahydropyrimido[4,5-g]quinoline.

10. A compound according to claim 1 in which R is $C_1$–$C_3$ alkyl or allyl.

11. A compound according to claim 1 in which R is H or CN.

* * * * *